United States Patent [19]
Cano et al.

[11] Patent Number: 5,695,511
[45] Date of Patent: Dec. 9, 1997

[54] SURGICAL INSTRUMENTS FOR MINIMALLY INVASIVE PROCEDURES

[75] Inventors: Gerald C. Cano, Pittsburgh; Jonathan E. Hottenstein, Sewickley, both of Pa.

[73] Assignee: Metamorphic Surgical Devices, Pittsburgh, Pa.

[21] Appl. No.: 346,571

[22] Filed: Nov. 29, 1994

[51] Int. Cl.[6] .................................................. A61B 17/00
[52] U.S. Cl. ........................... 606/170; 606/1; 606/167
[58] Field of Search ............................. 606/166, 167, 606/170, 180, 171, 174, 1, 205; 30/162

[56] References Cited

U.S. PATENT DOCUMENTS

| 5,090,956 | 2/1992 | McCoy . |
| 5,114,402 | 5/1992 | McCoy . |

OTHER PUBLICATIONS

"Micro/Miniature Shape Memory Alloy Actuator" by Koji Ikuta, Proc. IEEE, (1990), pp. 2156–2161.

"Shape Memory Alloy Servo Actuator Ssytem With Electric Resistance Feedback and Application for Active Endoscope", by Koji Ikuta, Masahiro Tsukamoto and Shigeo Hirose, Proc. IEEE (1988), pp. 427–430.

Primary Examiner—Michael Powell Buiz
Assistant Examiner—William Lewis
Attorney, Agent, or Firm—Buchanan Ingersoll, P.C.; Lynn J. Alstadt

[57] ABSTRACT

A surgical cutter intended for use in endoscopic procedures utilizes at least one shape-memory-effect (SME) alloy actuator to move one or more blades or other surgical tips in a reciprocal, rotational, or scissors-type motion to incise or excise tissue. Such cutters have a cutter assembly, mounted in a shaft connected to a handle, with a blade or blades that are moved individually or in concert. The actuator is formed of one or more wire SME alloy loops and optional bias spring. Application of an appropriate voltage waveform in a specified time sequence causes each wire loop to contract and return to its original length. Each actuator is mechanically linked to the cutting blade or other surgical tip.

17 Claims, 5 Drawing Sheets

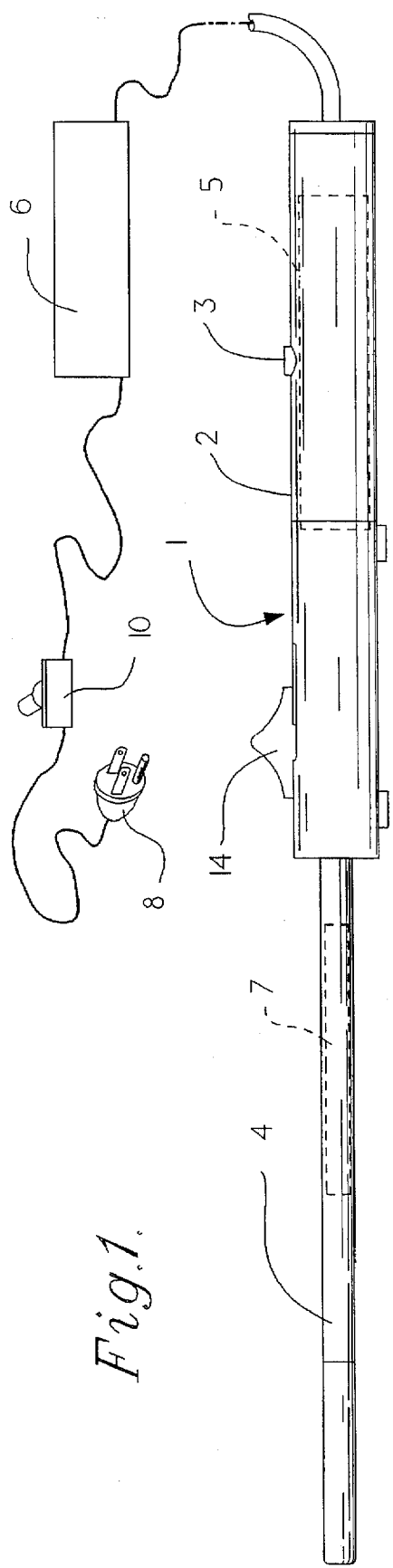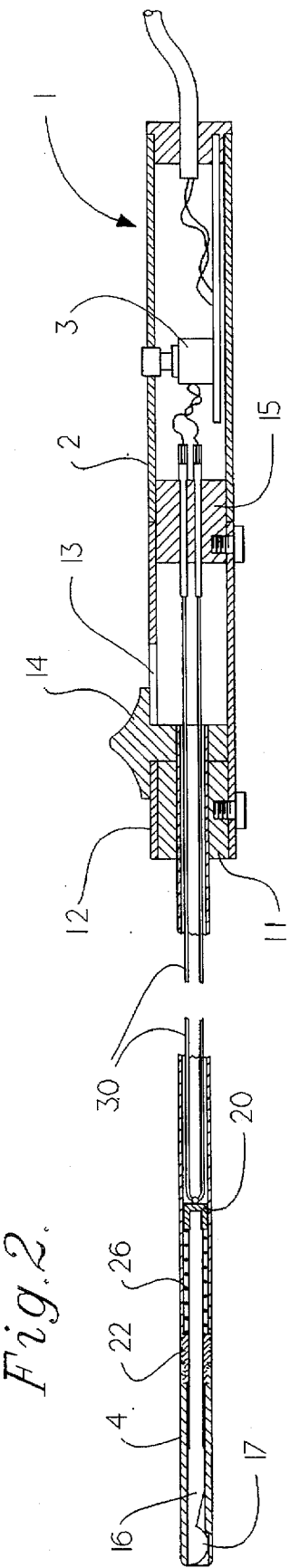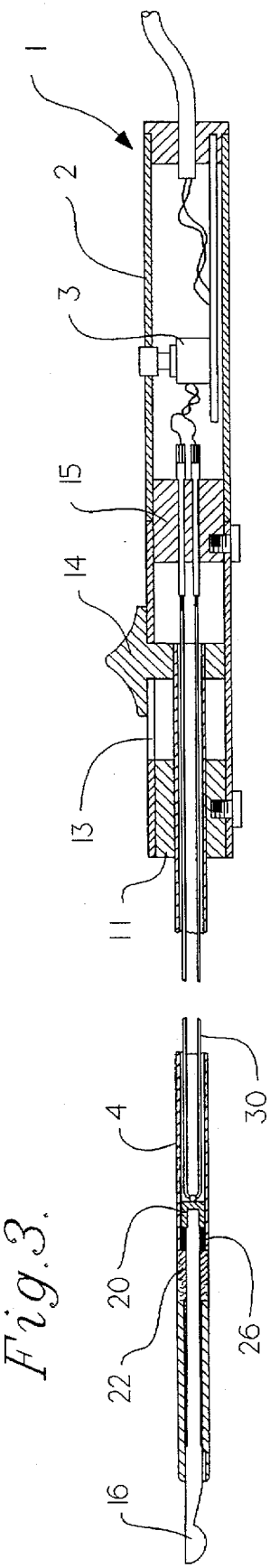
Fig.1.
Fig.2.
Fig.3.

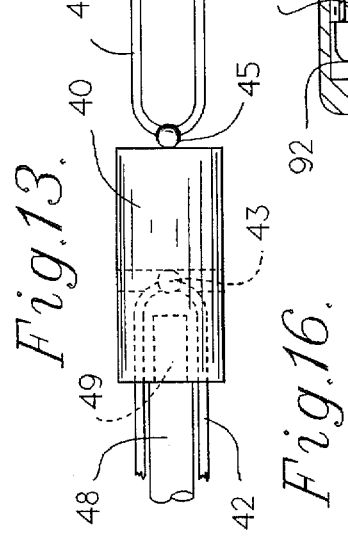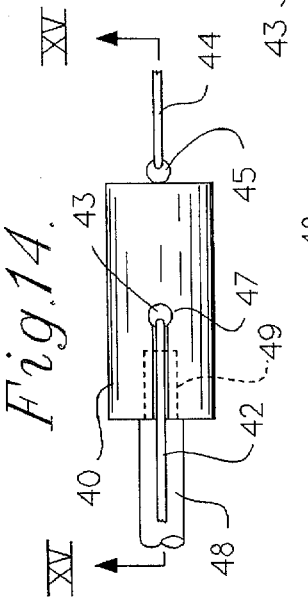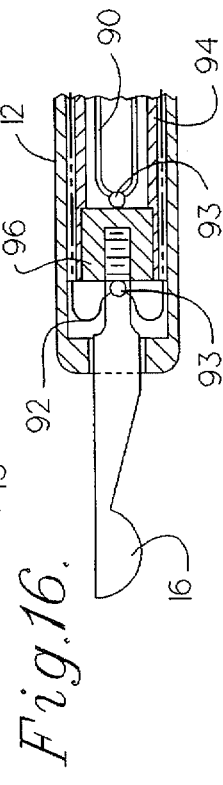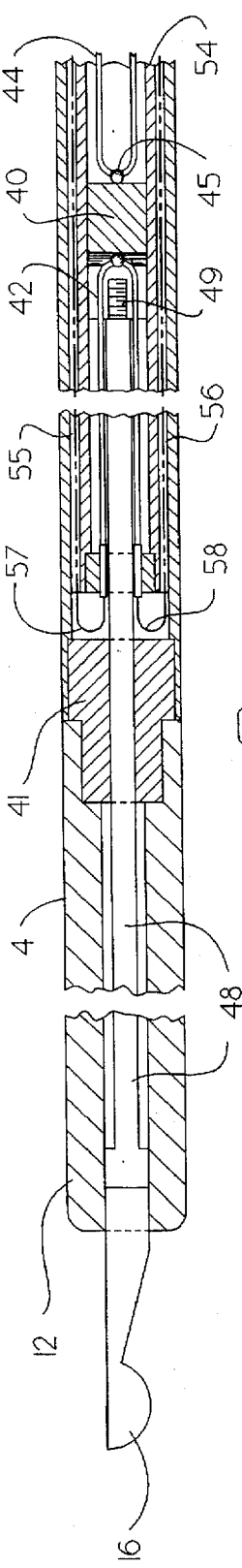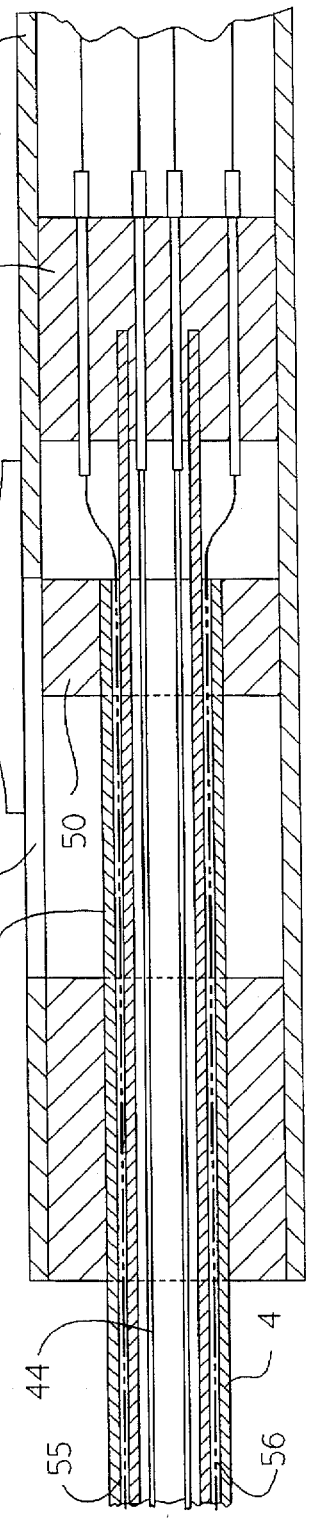

SURGICAL INSTRUMENTS FOR MINIMALLY INVASIVE PROCEDURES

TECHNICAL FIELD

This invention relates to surgical instruments used in minimally invasive procedures under endoscopic or fluoroscopic visualization and more specifically to devices used to cut tissue.

BACKGROUND ART

Surgical cutting of tissue is predominantly performed using devices with blades. Size and shape of the blades vary. The means of applying cutting motion to the blade also varies.

The simplest surgical cutting device is the common scalpel. It may be used to incise body surface tissue or excise internal organs or structures. The surgeon places the blade on the tissue to be cut, applies appropriate pressure, and moves the blade across the tissue. Cutting on the body surface is easier to accomplish as such movement can be done relatively free of obstructions. Surgical procedures that involve the cutting of internal organs and body tissue include the making of an access incision and pathway to enable the surgeon to reach the affected area. In part, because cutting requires the blade edge to be moved across the tissue, surgical procedures have required large incisions to expose internal organs and structures so the surgeon can impart the cutting motion to the blade.

Many surgical procedures have been developed in which a small incision is made and an endoscope is inserted through that incision to the surgical site. Then a cutting tool or other surgical instrument is inserted through a lumen in the endoscope or through another small incision to perform the surgical procedure. Because the use of an endoscope or similar instrument requires a relatively small incision less trauma occurs and healing proceeds more rapidly. Consequently, doctors prefer to use this type of surgical procedure whenever possible.

Several cutting tools have been developed for endoscopic surgery. The harmonic scalpel was developed for cutting of internal tissue. Its primary use is in laparoscopic cholecystectomy. This scalpel is positioned at the surgical site through a small incision. A piezoelectric crystal imparts high frequency vibratory motion to the blade. For instance, the blade movement is on the order of tens of microns and typically occurs at about 50 kilohertz. Tissue to be cut with this device must be held under tension; otherwise, the scalpel is ineffective. The vibratory motion also acts to coagulate blood through the generation of heat.

Another means to cut tissue in laparoscopic cholechsystectomy is with small scissors blades mounted to a long narrow extension handle. Cutting, that is, opening and closing of the small blades, is provided by hand motion as with standard scissors.

A shaver is used in arthroscopic meniscectomy to manicure the meniscus in a joint such as the knee or shoulder. It is comprised of a rotating tube within a tube. A section is removed from the tip of the inner tube; the resulting edges that are left after removal of the section are sharpened. A similar section is removed from the tip of the outer tube. The tip is placed on the meniscus, the inner tube rotating within the outer tube to shave small fragments from the meniscus. Usually, the fragments are sucked down the inner tube under vacuum. It is not unusual for fragments to clog the inner tube. Continuous irrigation of the joint slowly flushes fragments from the joint.

A "basket" is also used in arthroscopic meniscectomy of a joint such as the knee or shoulder. It consists of small upper and lower jaws that bite or nibble at the edge of the meniscus, creating small fragments that must be flushed from the joint by irrigation.

All of the endoscopic cutting tools require that the surgeon provide the cutting motion and require the tissue being cut to be held in tension. Thus, there is a need for a surgical cutting device which does not suffer from these problems and can be used in endoscopic surgical procedures.

There is a class of alloys known as shape-memory-effect alloys or "SME alloys" which can be formed into wire structures that change when heated. This class of alloys includes certain titanium-nickel alloys, copper-aluminum-nickel alloys and copper-aluminum-zinc alloys. The most well-known SME alloy is sold under the trademark NITINOL.

The art has proposed to use SME alloys in catheters, grippers and endoscopes. The catheters and endoscopes which use SME alloys are constructed to have an initial shape. The SME alloy portion of the device is heated by passage of an electrical current causing the device to take a different shape. SME alloy springs have been connected to jaw type grippers for medical and industrial use. Electrical current is passed through the springs causing them to contract and close the gripper. Examples of these uses of SME alloys are described in U.S. Pat. Nos. 5,090,956 and U.S. Pat. No. 4,114,402 and by Ikuta et al. in "Shape Memory Alloy Servo Actuator System with Electric Resistance Feedback Application to Activate Endoscope," *Proc. IEEE Int. Conf. Robotics and Automation,* Philadelphia, U.S.A, p. 427 (1988) and "Micro/Miniature Shape Memory Alloy Actuator," *Proc. IEEE,* p. 2156 (1990). Prior to the present invention the art has not recognized that SME alloys could be used for actuators to impart reciprocal or rotational motion to a cutting tool.

SUMMARY OF THE INVENTION

The present surgical cutter is intended for use in endoscopic procedures and utilizes at least one shape-memory-effect (SME) alloy actuator to move one or more cutting edges of one or more blades or other surgical tip across or through tissue to incise or excise the tissue. Such cutters have a cutter assembly, mounted in a shaft connected to a handle, with a blade or blades that are moved individually or in concert by the actuator formed of one or more SME alloy loops powered electrically by application of the appropriate voltage waveform in the specified time sequence. Each actuator is mechanically linked to the surgical tips. Motion may be, but is not limited to, a reciprocating linear or circular motion or a scissoring motion. The cutter assembly is at the end of a shaft to facilitate insertion into the body.

This cutting tool is a simple, small cutting device for endoscopic surgical procedures that imparts a cutting motion to its blade for the surgeon. A surgeon using this tool has finer positioning and cutting control which improves surgical safety by automatic repositioning of the blade thereby limiting any errant movement of the blade.

Design simplicity, the resultant reduced size, and finer control are achieved by the use of an actuator or actuators incorporating a shape-memory-effect (SME) alloy to impart a cutting motion to the blade.

BRIEF DESCRIPTION OF THE DRAWINGS

FIG. 1 is a side view of a first present preferred embodiment of our surgical cutting device for use with an endoscope in minimally invasive surgery.

FIG. 2 is a cross sectional view of the embodiment shown in FIG. 1.

FIG. 3 is a cross sectional view similar to FIG. 2 after the blade of the cutter assembly has been exposed.

FIG. 11 is a cross sectional view of the tip portion of a fifth present preferred embodiment of our cutting device.

FIG. 12 is a cross sectional view of the handle portion of the embodiment shown in FIG. 9.

FIG. 13 is a side view of the piston portion of the actuator used in the embodiment of FIGS. 11 and 12.

FIG. 14 is a top plan view of the piston shown in FIG. 11.

FIG. 15 is a cross sectional view taken along the line XV—XV in FIG. 14.

FIG. 16 is a sectional view of the top of a sixth preferred embodiment of our surgical cutting device.

DETAILED DESCRIPTION OF THE INVENTION

Figure 4:
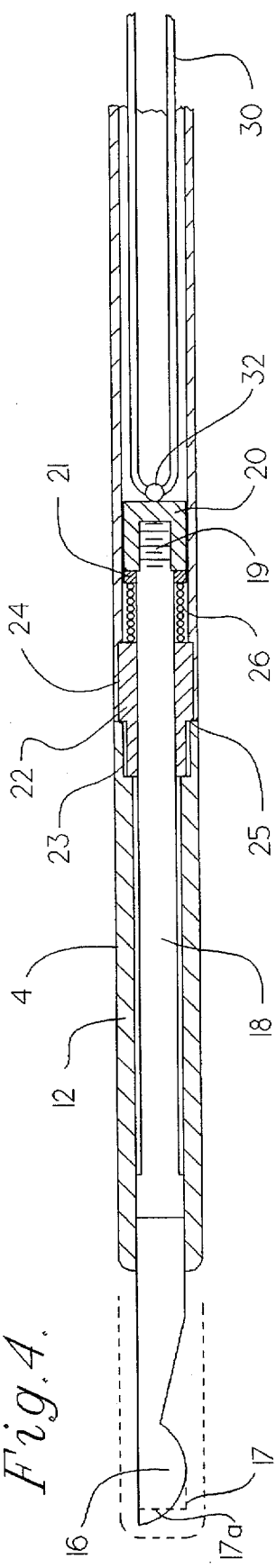
FIG. 4 is an enlarged cross-section of the cutter tip shown in FIG. 3 before the actuator has been energized.
Figure 5:
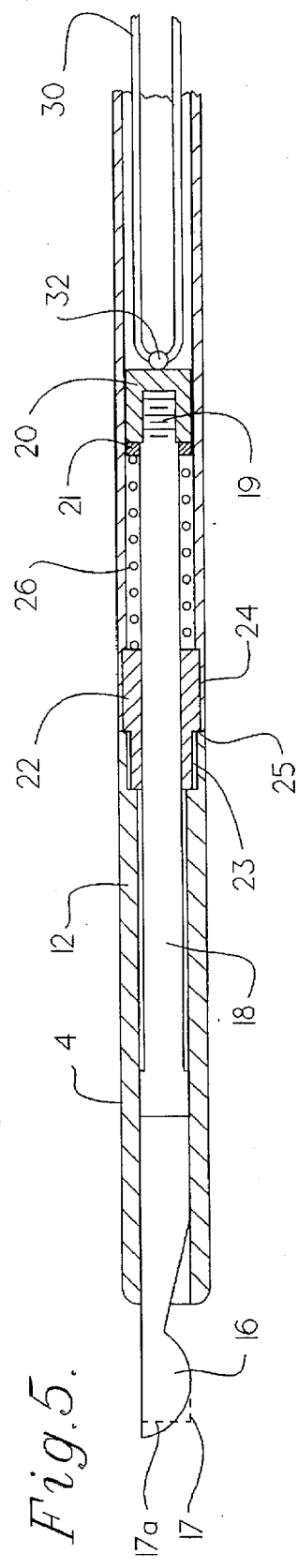
FIG. 5 is an enlarged cross-section of the cutter tip shown in FIG. 4 after the actuator has been energized and the blade has fully retracted.

A shape-memory-effect alloy actuator in our cutting device provides the appropriate reciprocating, scissoring or rotational motion over a fixed distance to a variety of tips.

Functionally, an actuator may either create forceful motion followed by passive less forceful, return motion, or create forceful motion in one direction followed by a forceful return motion. Forceful motion is created by heating a SME element until its temperature increases above its transition temperature so that the alloy lattice transitions from martensite, a soft form of alloy, to austenite, a hard form of alloy. The lattice change from martensite to austenite causes a dimensional change in the SME element that generates force. However, when temperature falls below transition, the resulting change from austenite to martensite does not produce a dimensional change that can generate force. Consequently, a bias force is applied to the SME element to return it to its original dimensions.

The SME elements in one type of actuator may be either an anchored wire or spiral spring; the bias force generator may be an appropriately sized spring, normally not made of SME alloy. The SME elements in a second type of actuator may be either two opposing anchored wires or two opposing spiral springs.

An actuator operates on a heating and cooling cycle established by the power supply. Joule heating raises the temperature of the SME elements. During that part of the cycle when current is on, the temperature of an SME element rises to slightly above its transition temperature so that the alloy lattice changes from martensite to austenite. During that part of the cycle when current is off, the temperature of the element falls to below transition allowing the lattice structure to revert back to martensite.

Either actuator can be used to power a cutter. Cutting action occurs when the same element is powered. Depending on blade configuration, the second actuator can provide cutting action in two directions. The first actuator can provide cutting action only in one direction; no cutting is done during reset of the cutter by the bias spring. In both, the degree of motion is constrained by the actuator.

The cycle time, that is, the time for the cutter blade or blades to first move, return to original position, and then be able to initiate another sequence is dependent upon heating and cooling rates. Active heating with passive cooling restricts cycle time to about three seconds minimum.

As shown in FIG. 1, our cutting device 1 basically consists of a handle assembly 2, shaft 4 which contains a cutter blade, a power supply 6 and an actuator which may be within the handle 2 as indicated by chain line box 5 or within the shaft 4 as indicated by chain line box 7 or extend through both the shaft and the handle as in the first embodiment shown in FIGS. 2 thru 5. An electrical cord 8 with switch 10 is provided to connect the power supply to a standard 110/220 outlet. The power supply 6 provides a timed sequence of DC pulses or high frequency AC pulses to the actuator. We prefer to use a shaft 4 having an outer diameter of 4.75 mm or less. If desired, a radio opaque marker not shown may be placed on the tip of the shaft assembly.

The first present preferred embodiment is shown in FIGS. 2 thru 5. This embodiment utilizes an actuator consisting of a NITINOL wire element 30 to provide a forceful cutting motion to blade 16 and a bias spring 26 to return the NITINOL wire 30 to its original length as the spring returns to its original position. The shaft assembly is comprised in an outer sheath 12 which passes through spacer 11 and is connected to a slide 14 positioned within the handle 2. This can be seen in FIGS. 2 and 3. A slot 13 is provided within the handle 2 to enable the outer sheath to be retracted into the handle. A blade 16 having at least one cutting surface 17 is located at the distal end of the shaft assembly. If desired, the cutting edge could be transverse to the longitudinal axis of the blade as indicated by chain line 17a or otherwise oriented. The blade 16 is attached to a connecting rod 18 which is fitted into an insulated connector 20 to form a cutter assembly. The proximal end 19 of the connecting rod 18 is sized to fit into the connector 20. We prefer to provide a bushing 22 having a minor diameter 23, major diameter 24 and shoulder 25 therebetween. The inner surface of the sheath 12 is sized and configured to have a mating shoulder. If desired, threads could be placed on the mating surfaces of bushing 22 and the surface of connecting rod 18. The threads would then cause the cutter assembly to rotate as it advances and retracts. A spring 26 is attached between bushing 24 and collar 21 on connector 20. When the shaft is retracted from the position shown in dotted line in FIG. 4 to expose the blade, spring 26 will be relaxed. Alternatively, the cutting device could be configured so that the distal end of spring 26 is connected to the connecting rod and the proximate end is attached to the shaft. Movement of the blade is caused by actuator element 30 made of SME alloy. The loop 30 is attached to connector 20 by fastener 32 which is crimped to the distal end of the loop and attached to the connector 20. One suitable method of attachment is to provide a threaded shaft (not shown) on the crimped fastener 32 which screws into a suitable threaded cavity (not shown) within connector 20. Spacer 15 is provided to hold the loop 30 in place and can also serve as a heat sink to speed cooling. If desired, additional means could be provided to improve heat transfer from the loop during cooling.

After the sheath has been retracted to expose the blade as shown in FIG. 3, the surgeon presses switch 3 in handle 2. This causes current to flow through the SME alloy loop 30. As the electrical current heats the loop, the alloy lattice undergoes a change from martensite to austenite structure. This shrinks the length of the loop from about four percent to eight percent in overall dimensions. As the loop shrinks, it pulls the blade forcefully toward the handle. That movement also causes spring 26 to stretch. When the current flow stops the alloy cools and is returned to its original length. Since spring 26 is under tension it will pull the blade away from the handle as the loop cools. Thus, reciprocal movement can be obtained by applying timed sequences of current to the loop 30. It should be apparent that the extent of blade movement is dependent upon the length and cross-section of loop 30. The level of force exerted corresponds to the diameter of the wire forming the loop. We have found that a loop of approximately eight inches (20 cm) in length and 6 mil. in diameter will provide movement of about 0.4 to 0.5 inches (1 cm). Cycle time is about 2.5 to 3 seconds.

Figure 6:
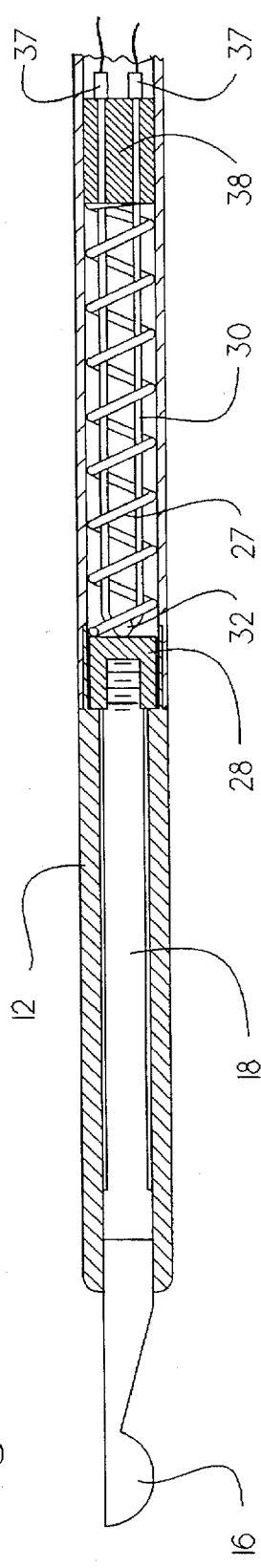
FIG. 6 is an enlarged cross-sectional view similar to FIG. 4 showing a second preferred embodiment.

The spring can alternatively be spiraled around the SME element as shown in FIG. 6. This embodiment utilizes an actuator consisting of a NITINOL wire element 30 to provide a forceful cutting motion to a blade 16 and a bias spring 27 to return the NITINOL wire to its original length and also reposition the blade to its original position. The NITINOL wire element passes through an insulated connector 28 on the shaft of the blade 16. The ends of wire 30 are attached to crimp-on fasteners 37 that are anchored in a spacer 38 to hold the wire in place. Joule heating raises the temperature of the NITINOL wire 20 above its transition temperature causing the wire 30 to shorten in length, thus forcefully pulling the blade 16 toward the spacer 38.

Figure 17:
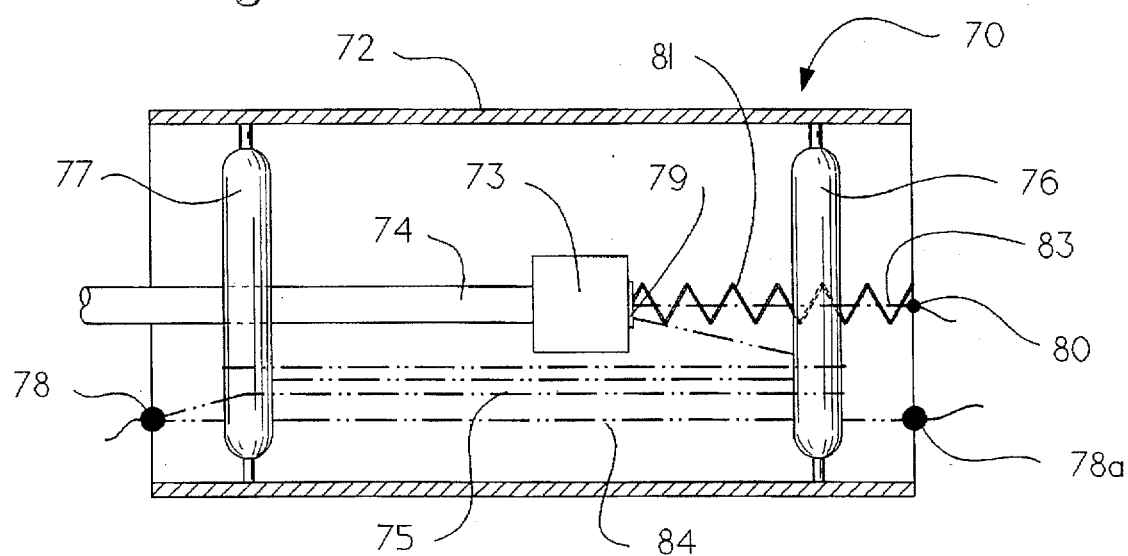
FIG. 17 is a sectional view of an actuator module for a seventh preferred embodiment of our surgical cutting device.
Figure 18:
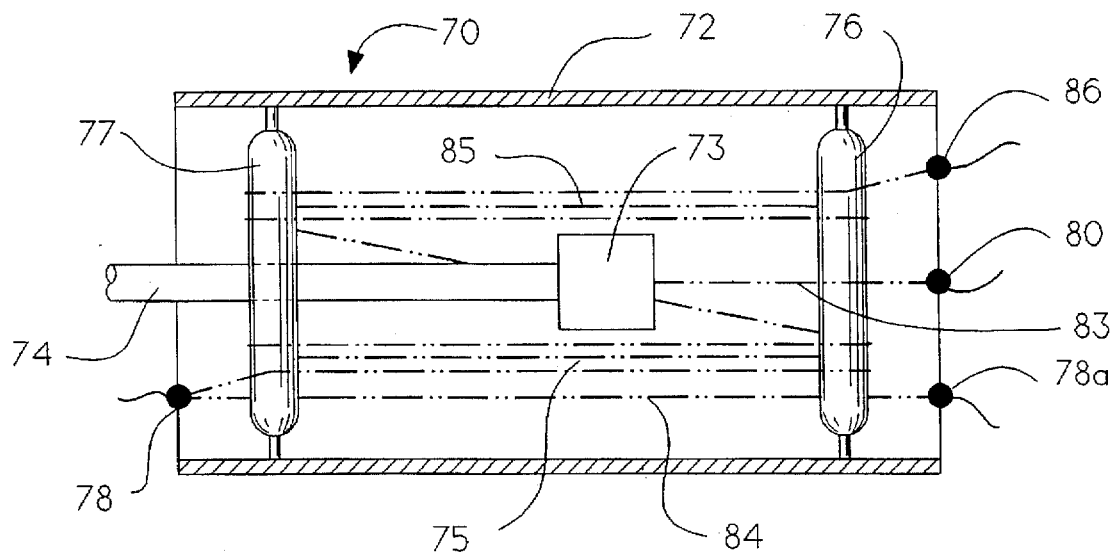
FIG. 18 is a sectional view of a second actuator module.

Although we have shown loop 30 to be a generally U-shaped configuration, the loop can also be spiraled into a helix or spring-like configuration or wound as shown in the embodiments of FIGS. 17 and 18. By controlling the windings of loop 30 we can determine the distance over which the blade will be moved.

Figure 7:
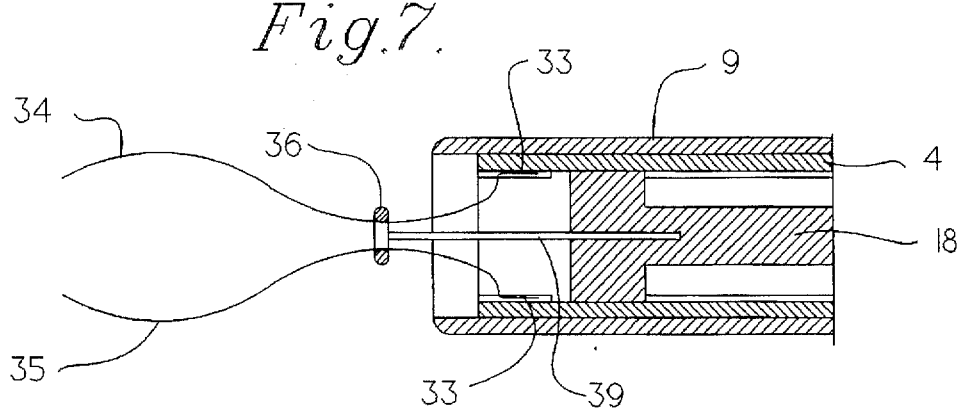
FIG. 7 is an enlarged cross-sectional view showing the distal end of a third present preferred embodiment having a forceps type cutting tip shown before the actuator has been energized.
Figure 8:
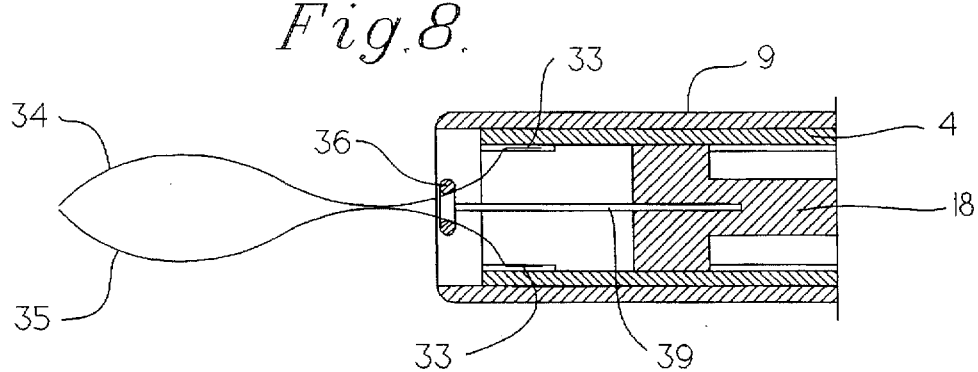
FIG. 8 is an enlarged cross-section of the cutter tip shown in FIG. 7 after the actuator has been energized and the forceps have been closed.

The distal end of a third present preferred embodiment of our cutting device is shown in FIGS. 7 and 8. Except for the cutter assembly at the distal end, this embodiment is similar to the first embodiment shown in FIGS. 2 thru 5. In the embodiments of FIGS. 7 and 8 proximate ends 33 of a pair of wires 34 and 35 are fitted within slots in shaft 4. A moveable outer sheath 9 surrounds shaft 4. A collar 36 fits over wires 34 and 35 and is attached by rod 39 to connecting rod 18 to form a jaw-type cutter. Current passing through the SME loop attached to connecting rod 18 pulls the rods 18 and 39 into the shaft, pulling the collar 36 inward along wires 34 and 35. As the collar moves inward the wires close and grasp tissue therebetween tearing or cutting the tissue. The tips of the wires could be dull or sharp. By maintaining current flow through the SME loop we can keep the jaw closed.

Figure 9:
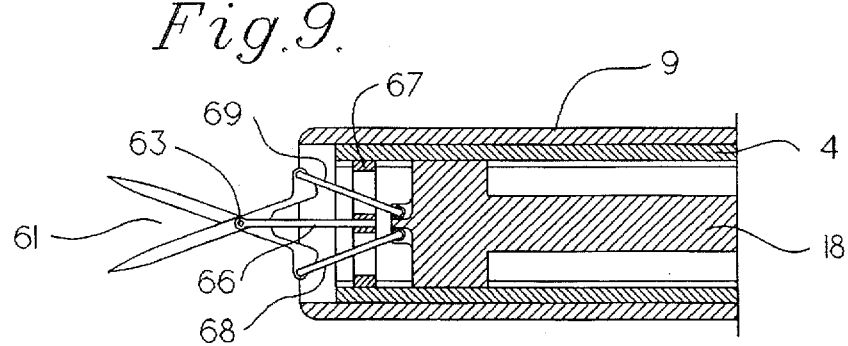
FIG. 9 is an enlarged cross-sectional view showing the distal end of a fourth present preferred embodiment having a scissors type cutting tip shown before the actuator has been energized.
Figure 10:
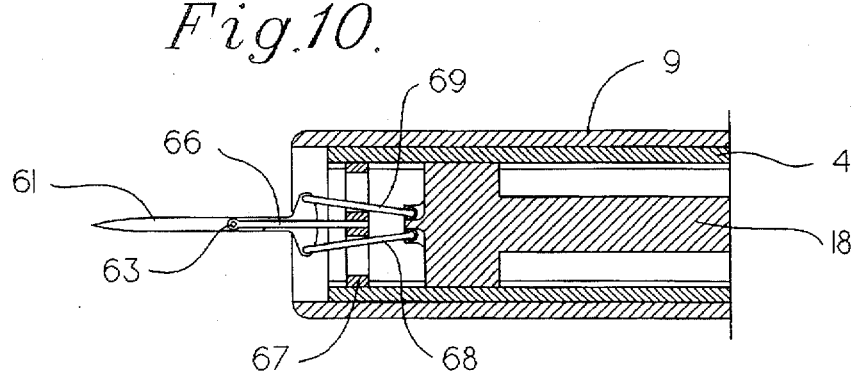
FIG. 10 is an enlarged cross-section of the cutting tip shown in FIG. 9 after the actuator has been energized and the scissors have been closed.

The surgical tip 61 in the fourth embodiment shown in FIGS. 9 and 10 provides a scissors-type action. Stabilizer rod 66 extends from the pivot point 63 of scissors 61 to collar 67 which is fixed relative to shaft 4. Tie rods 68 and 69 extend from the proximate ends of scissors 58 to connecting rod 18. When the SME activator pulls connecter rod 18 toward the handle tie rods 68 and 69 will move inward to close the scissors 58. Preferably, a movable outer sheath 9 is provided around shaft 4.

A fifth present preferred actuator arrangement is shown FIGS. 11 thru 15. This actuator is connected to the cutting assembly in a manner similar to that shown in FIGS. 2 thru 5. A blade 16 is connected to a connecting rod 48 having a threaded end 49 which fits into a suitable cavity in piston 40. The cutting assembly is fitted within sheath 12 having a bushing 41 which supports connecting rod 48. As shown in FIG. 12 sheath 12 is connected to slide 50 which slides within a slot 51 in the handle 52.

As shown in FIGS. 13, 14 and 15 the actuator is comprised of piston 40 having opposing SME alloy loops 42 and 44 connected to opposite ends of the piston. Loop 44 is connected by connector 45 in the same manner as the loop is attached in the first embodiment. A longitudinal slot 46 is provided in piston 40 to receive the U-shaped end of loop 42. A ball 43 is crimped on the end of that loop. Transverse slot 47 is sized to receive the ball 43. When the loop 42 is positioned as shown in FIGS. 10 and 12 the ball 43 will restrain the loop 42 from being pulled from the piston 40. Thus, as loop 42 shrinks in response to current flow through the loop it will pull the piston toward the distal end of the device. Similarly, when loop 44 shrinks by application of a current it will pull the piston in the opposite direction toward the handle. Thus, by alternately energizing loops 42 and 44 we can achieve a reciprocating movement of the piston as can be seen in FIGS. 9 and 10. A sleeve 54 is provided within the shaft assembly 4. Sleeve 54 is sized to define channels 55 and 56 between the sheath 12 and the sleeve 54. The channels are sized to receive wires 57 and 58 which are connected to the distal end of loop 42. We prefer to provide a spacer 53 within the handle to maintain separation between wires 57 and 58 and loop 44.

A double loop actuator could also be connected directly to the end of the blade as shown in FIG. 16. This actuator consists of two NITINOL wire elements 90 and 92 to provide forceful motion in two directions to a blade 16. The NITINOL wire 92 passes between the sheath 12 and insulated sleeve 94. The ends of the wires 90 and 92 are attached to crimp-on fasteners 93 that are anchored in spacer 96 to which blade 16 is attached. Joule heating raises the temperature of wire 90 above its transition temperature while wire 92 is below its transition temperature, shortening wire 90; the forceful motion generated pulls blade 16 into the sheath and elongates wire 92. Wire 90 is then allowed to cool below its transition temperature. Joule heating then raises the temperature of wire 92 above its transition temperature, shortening wire 92, the forceful motion generated pulls blade 16 out of the sheath and elongates wire 90. Each NITINOL wire element can be replaced by a NITINOL spiral spring element. NITINOL spring elements cannot generate as much force as a wire element of the same gage wire; however, they can cause a greater displacement than a wire element.

The cutter assemblies in FIGS. 2 thru 16 are shown with actuators composed of discrete components. However, each actuator can be modularized so that each NITINOL element and any needed bias springs are contained and mounted within a module with all electrical contacts mounted on an external surface of the module. A representation of one such modular actuator capable of powered motion in one direction is shown in FIG. 17. The actuator 30 consists of a cylindrical case 72 that houses a sliding piston 73 with a configuration rod 74 extending from a piston 73 through the housing 72. A NITINOL wire element 75 is wound around rollers 76 and 77 to provide sufficient length of NITINOL wire for the desired amount of movement of the piston 73. The NITINOL wire element 75 is anchored to the housing 72 at electrical contact 78 that passes through the housing 72 and is attached to the piston 73 at connector 79.

We prefer to provide another connector 78 at the opposite end of the module and copper wire 84 between connectors 78 and 78a. Copper wire 83 running from connector 79 to electrical connector 80 completes the current carrying circuit for heating the NITINOL wire element 75. A bias spring 81 resets the position of the piston and elongates the NITINOL wire element 75. A blade or connecting rod (not shown) is attached to rod 74 extending from piston 73. The power supply (not shown) is connected to connectors 80 and 78 or 78a. This module could be placed in the handle or shaft of the device as indicated by blocks 5 and 7 in FIG. 1.

A second actuator module is shown in FIG. 18. This module is similar to the module of FIG. 17 and like parts have the same reference number. In the module the bias spring has been replaced with a second NITINOL wire element 85 and associated electrical connector 86. As in the embodiment of FIGS. 8 thru 12, the wire elements 75 and 85 are alternately energized to provided reciprocating motion of the blade.

Although we have shown three types of cutting tips, those skilled in the art will recognize that other types of cutting tips or grasping tips could be used. It should also be recognized that one could use a chisel type tip or pointed tip for some applications as for example breaking up kidney stones.

The device could operate on battery power rather than AC current. Although we have shown our power supply separate from the handle it is also possible to put the power supply in the handle.

Although we have disclosed and claimed certain present preferred embodiments of our cutting device, it should be distinctly understood that our invention is not limited thereto, but may be variously embodied within the scope of the following claims.

We claim:

1. A surgical device comprising:
   a) a power supply capable of providing a sequence of pulses to an actuator assembly;
   b) a handle having a switch therein;
   c) at least one electrical conductor connected between the power supply and the switch;
   d) a tubular shaft assembly attached to and extending from the handle;
   e) an actuator, mounted in at least one of the handle and the shaft consisting of at least one shape-memory-effect alloy element, the at least one shape-memory-effect alloy element having a distal end and a proximal end, the proximal end electrically connected to the switch so that when the switch is placed in an "ON" position, at least one shape-memory-effect alloy element is electrically connected to the power supply; and
   f) at least one surgical tip mechanically linked to the actuator so that the actuator causes movement of the surgical tip when the switch is placed in an "ON" position assembly.

2. The device of claim 1 also comprising a connecting rod between the surgical tip and the actuator.

3. The device of claim 1 wherein said tubular shaft is slidably attached to the handle and sized to sufficiently cover the surgical tip when in an extended position and to retract and expose the surgical tip when in a retracted position.

4. The device of claim 3 also comprising a slide mechanism within the handle and attached to the shaft to enable a user of the device to move the shaft between the extended position and the retracted position.

5. The device of claim 1 also comprising connector means connecting the surgical tip to the actuator in a manner so that the surgical tip can be rotated relative to the tubular shaft.

6. The device of claim 1 wherein the actuator is comprised of two opposing shape-memory-effect alloy elements both of which are mechanically linked to the surgical tip.

7. The device of claim 6 also comprising a piston to which the shape-memory-effect alloy elements and surgical tip are attached.

8. The device of claim 6 also comprising a piston to which the shape-memory-effect alloy elements are attached and a connecting rod attached between the piston and the surgical tip.

9. The device of claim 6 also comprising connector means connecting the surgical tip to the actuator in a manner so that the surgical tip can be rotated relative to the tubular shaft.

10. The device of claim 6 wherein at least one of the two shape-memory-effect alloy elements is one of a titanium-nickel alloy, a copper-aluminum-nickel-alloy and a copper-aluminum-zinc alloy.

11. The device of claim 6 wherein the surgical tip is comprised of at least one blade.

12. The device of claim 6 wherein the actuator is a removable module.

13. The device of claim 6 wherein the surgical tip can undergo reciprocating linear motion relative to the tubular shaft.

14. The device of claim 1 wherein the at least one shape-memory-effect alloy element is comprised of one of a titanium-nickel alloy, a copper-aluminum-nickel-alloy and a copper-aluminum-zinc alloy.

15. The device of claim 1 wherein the surgical tip is comprised of at least one blade.

16. The device of claim 1 wherein the actuator is a removably mounted in at least one of the handle and the shaft.

17. The device of claim 1 wherein the surgical tip can undergo reciprocating linear motion relative to the tublar shaft.

* * * * *